US 8,861,816 B2

(12) United States Patent
Lang et al.

(10) Patent No.: US 8,861,816 B2
(45) Date of Patent: Oct. 14, 2014

(54) METHOD AND APPARATUS FOR PRESCRIPTION MEDICATION VERIFICATION

(75) Inventors: David A. Lang, Commerce Township, MI (US); David A. Yanez, Livonia, MI (US); Nelson D. Tarr, Natick, MA (US); Chris S. Burt, Plymouth, MI (US)

(73) Assignee: Illinois Tool Works Inc., Glenview, IL (US)

( * ) Notice: Subject to any disclaimer, the term of this patent is extended or adjusted under 35 U.S.C. 154(b) by 204 days.

(21) Appl. No.: 13/310,971

(22) Filed: Dec. 5, 2011

(65) Prior Publication Data

US 2013/0142406 A1    Jun. 6, 2013

(51) Int. Cl.
*G06K 9/00* (2006.01)

(52) U.S. Cl.
USPC .......................................... 382/128; 382/192

(58) Field of Classification Search
None
See application file for complete search history.

(56) References Cited

U.S. PATENT DOCUMENTS

| | | | |
|---|---|---|---|
| 4,446,481 A | | 5/1984 | Edamatsu et al. |
| 4,597,091 A | | 6/1986 | Blake |
| 5,111,516 A | * | 5/1992 | Nakano et al. ............... 382/156 |
| 5,422,831 A | | 6/1995 | Misra et al. |
| 5,440,648 A | | 8/1995 | Roberts et al. |
| 5,558,231 A | | 9/1996 | Weier |
| 5,671,262 A | | 9/1997 | Boyer et al. |
| 5,684,892 A | * | 11/1997 | Taguchi ........................ 382/193 |
| 5,893,095 A | * | 4/1999 | Jain et al. ............................. 1/1 |
| 6,529,892 B1 | * | 3/2003 | Lambert ......................... 706/55 |
| 6,535,637 B1 | * | 3/2003 | Wootton et al. ............... 382/190 |
| 6,610,973 B1 | | 8/2003 | Davis, III |
| 7,570,786 B2 | * | 8/2009 | Ateya ............................ 382/103 |
| 7,599,516 B2 | | 10/2009 | Limer et al. |
| 2005/0111724 A1 | * | 5/2005 | Macy et al. ................... 382/141 |
| 2006/0045312 A1 | * | 3/2006 | Bernstein et al. ............. 382/103 |
| 2006/0215884 A1 | * | 9/2006 | Ota ................................ 382/118 |
| 2007/0189597 A1 | * | 8/2007 | Limer et al. .................. 382/153 |

FOREIGN PATENT DOCUMENTS

EP    0371881    6/1990

* cited by examiner

*Primary Examiner* — Bhavesh Mehta
*Assistant Examiner* — Siamak Harandi
(74) *Attorney, Agent, or Firm* — Nelson Mullins Riley & Scarborough LLP

(57) ABSTRACT

A method of processing graphical image data representing optically scanned medication-related units may include receiving image data generated responsive to disposal of the units on a tray disposed a distance from an image acquisition component, the image data including data indicative of visually observable features of the units disposed on the tray. The method further includes comparing at least two features among the visually observable features from the image data to reference data indicative of corresponding features of reference units. The reference data is selected for comparison based on an identification of the reference data as corresponding to a prescription being processed. The reference data includes data indicative of features of the reference units extracted from images captured using hardware corresponding to hardware used to generate the image data. The method further includes generating a likelihood rating for each of the at least two features based on the comparing.

16 Claims, 12 Drawing Sheets

METHOD AND APPARATUS FOR PRESCRIPTION MEDICATION VERIFICATION

TECHNICAL FIELD

Example embodiments generally relate to medication verification systems and, more particularly, relate to optically based counting machines.

BACKGROUND

The number of pharmacies in the United States is quite large, and continues to grow. These pharmacies range in size and sophistication from very large pharmacies that employ robotic devices to fill prescriptions in an almost entirely automated fashion to relatively small pharmacies that employ manual methods to fill prescriptions. In between these extremes, thousands of pharmacies also employ a number of semi-automated prescription filling mechanisms. Filling prescriptions inherently includes counting the number of pills to be issued to ensure that the number of pills prescribed is matched. This counting may be done manually or automatically in corresponding ones of the aforementioned prescription filling mechanisms.

In manual counting, a pharmacist or assistant (a dispensing agent) reviews a prescription, finds the corresponding stock bottle, pours a number of units from the stock bottle, typically onto a specially-configured tray, then counts out the prescribed number of units, decanting these into a receiver bottle and returning any remaining units to the stock bottle. The receiver bottle is labeled with appropriate information, such as the prescriber's name, the name and dosage of the prescription, usage instructions, dates, and the like. This procedure is comparatively slow, and can be cumbersome.

Weighing or counting scales can quicken dispensing while providing an accurate count. Such scales may, for example, use a reference weight to determine a count of pills or units of medication that are located on the scale. While generally accurate and faster than manual processes under some circumstances, a counting scale may not necessarily have any inherent provision for determining whether the pills or units disposed on the scales are actually the correct types of pills for filling the prescription. Moreover, pill counting scales rely upon having accurate pill weight information, but the actual pill weights often vary due to various causes.

Other counting systems, such as optical beam pour through systems, also referred to as tablet counters, may employ troughs and flow regulation to direct units past an optical detector, which counts the units as they slide past. Such devices, although they are employing vision based counting techniques, are not generally further employed to determine whether the pills counted are the correct pills. Thus, it may be desirable to improve automated, or semi-automated prescription filling devices to add a verification ability to ensure that the correct medication is being dispensed.

BRIEF SUMMARY OF SOME EXAMPLES

Some example embodiments may provide a machine vision counting and verification system. In this regard, for example, a counting device is provided that can use vision based techniques to confirm whether pills (or medication units) disposed on a tray are the correct pills for filling a given prescription. In some cases, the pills may initially be counted using a vision based counting system that counts pills disposed on a tray and exposed to a light. This counting technique may not necessarily be sensitive to the color of the pills, but may instead simply rely on the shadows cast by each pill in the image projected onto the vision sensor. Thereafter, some example embodiments may generate color image data based on an image taken while the pills are on the tray. The image data may then be analyzed based on a plurality of features of the pills in order to determine whether the features of the pills on the tray match known features for the medication to which the prescription being filled corresponds. The known features may be stored in a database that is built using image data that is gathered via images captured on the same type of machine as the counting device. Thus, potential inconsistencies in image resolution, context and scale may be avoided since the same quality of camera may be employed at the same distance from the pills in both the reference images from which the known features are extracted and the image data currently being analyzed.

In one example embodiment, a method of processing graphical image data representing optically scanned medication-related units is provided. The method may include receiving image data generated responsive to disposal of the units on a tray disposed a distance from an image acquisition component where the image data includes data indicative of visually observable features of the units disposed on the tray. The method may further include comparing, via processing circuitry, at least two features among the visually observable features from the image data to reference data indicative of corresponding features of reference units. The reference data may be selected for comparison based on an identification of the reference data as corresponding to a prescription being processed. The reference data may also include data indicative of features of the reference units extracted from images captured using hardware corresponding to hardware used to generate the image data. The method may further include generating a likelihood rating for each of the at least two features based on the comparing.

In another example embodiment, a prescription verification device for medication-related units is provided. The device may include a tray, an image acquisition component and an image processor. The tray may be disposed on a base unit to receive units. The image acquisition component may be disposed a distance from the tray. The image acquisition component may be configured to generate image data responsive to disposal of the units on the tray and the image data may include data indicative of visually observable features of the units disposed on the tray. The image processor may include processing circuitry configured to compare at least two features among the visually observable features from the image data to reference data indicative of corresponding features of reference units and generate a likelihood rating for each of the at least two features based on the comparison. The reference data may be selected for comparison based on an identification of the reference data as corresponding to a prescription being processed. The reference data may include data indicative of features of the reference units extracted from images captured using hardware corresponding to hardware used to generate the image data.

In another example embodiment, a computer program product for processing graphical image data representing optically scanned medication-related units is provided. The computer program product may include at least one computer-readable storage medium having computer-executable program code instructions stored therein, the computer-executable program code instructions comprising program code instructions for receiving image data generated responsive to disposal of the units on a tray disposed a distance from an image acquisition component where the image data includes data indicative of visually observable features of the units disposed on the tray. The computer-executable program code instructions may further include program code instructions for comparing, via processing circuitry, at least two features among the visually observable features from the image data to reference data indicative of corresponding features of reference units. The reference data may be selected for comparison based on an identification of the reference data as corresponding to a prescription being processed. The reference data may also include data indicative of features of the reference units extracted from images captured using hardware corresponding to hardware used to generate the image data. The computer-executable program code instructions may further include program code instructions for generating a likelihood rating for each of the at least two features based on the comparing.

Some example embodiments may improve the performance of a vision-based medication counting machine. Moreover, some embodiments may provide the operator with an improved ability to confirm that the pills on the tray are the correct pills to be used to fill a prescription.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Figure 1:
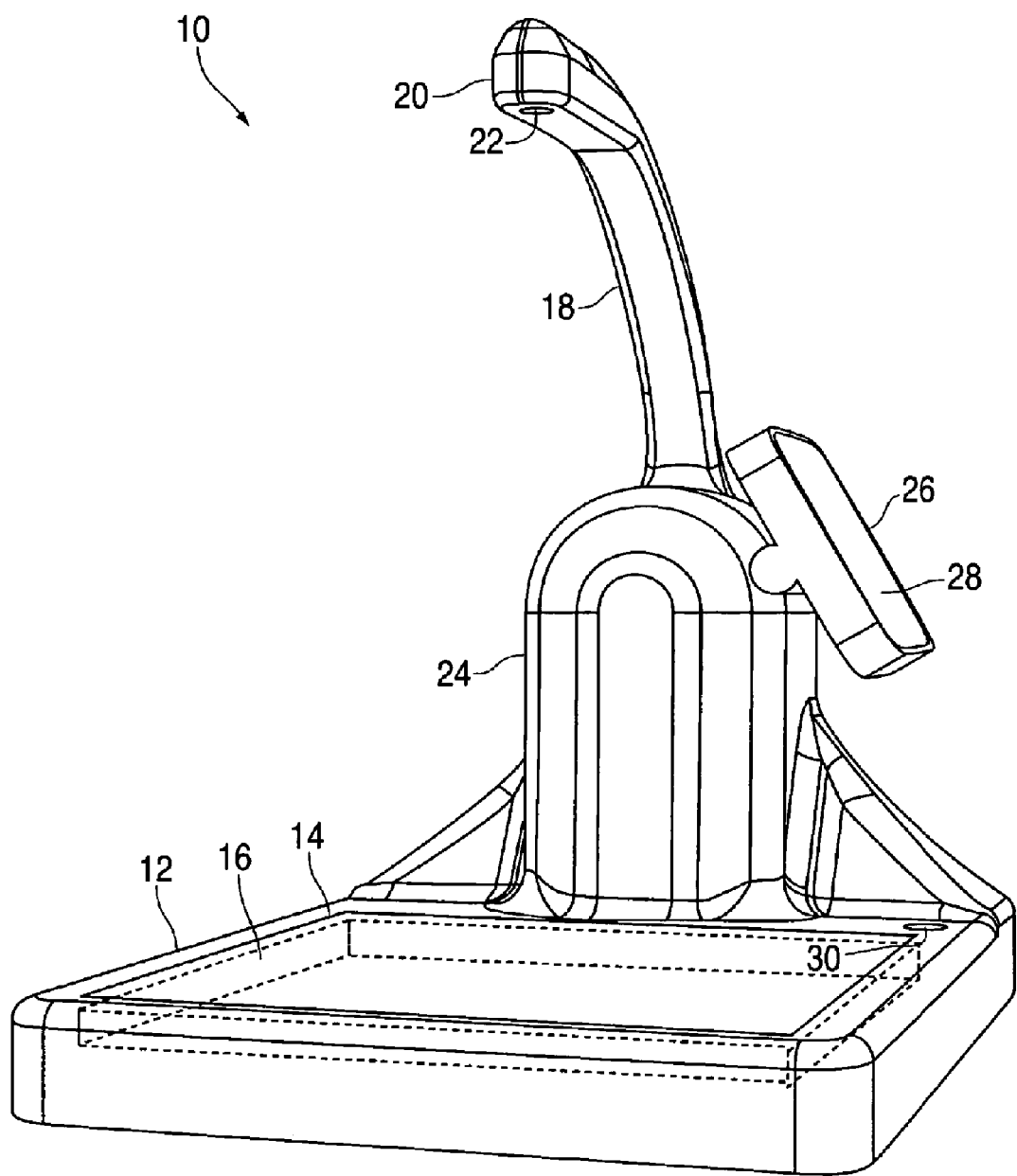
FIG. 1 is a perspective view of a counter and/or prescription verification device according to an example embodiment.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. Furthermore, as used herein, the term "or" is to be interpreted as a logical operator that results in true whenever one or more of its operands are true. As used herein, operable coupling should be understood to relate to direct or indirect connection that, in either case, enables functional interconnection of components that are operably coupled to each other.

Some example embodiments may improve the performance of a vision based counting machine. In this regard, for example, some embodiments may provide an apparatus that in some embodiments provides a self-contained unit counter with an illuminated stage, a camera, an image analyzer, a touch-screen display/operator interface, and a communication link to an external environment. In some embodiments, the unit counter may be configured to count pills and generate an image that can be used to verify that the pills on the stage are the correct pills to be used to fill a prescription as described in greater detail below.

FIG. 1 shows an example embodiment of a counter 10, having a base 12 for placement of the counter 10 on a surface. The counter 10 includes a stage 14 for positioning of units to be counted, an illuminator 16 oriented to provide illumination upward from the upper surface of the stage 14, and a neck 18, extending upward from the vicinity of the stage 14, that positions an imager head 20. The imager head 20 affixes and directs an image acquisition component (e.g., imager 22) toward the stage 14, permitting the imager 22 to acquire an image of any materials placed on the stage 14 and backlit by the illuminator 16. A circuit housing 24, configured to enclose electronic circuitry for operation of the counter 10, is, in the embodiment shown, at least partially integrated into the structure of the counter 10. However, the circuitry that controls operation of the counter 10 could be remotely located in some alternative embodiments.

An operator interface cluster 26, configured to provide display and input for a user, may also be integrated at least in part into the structure of the counter 10. The operator interface cluster 26 may include a display 28 that may be tiltable, and that may include touch screen function in some embodiments. A power control in the form of a low-profile pushbutton switch 30 may be positioned on a surface of the base 12. The counter 10 of FIG. 1 is in the form of a single, unitized apparatus including the base 12, the stage 14 and illuminator 16, the imager head 20, a processor contained within a circuit housing 24, and an operator interface 26.

Figure 2:
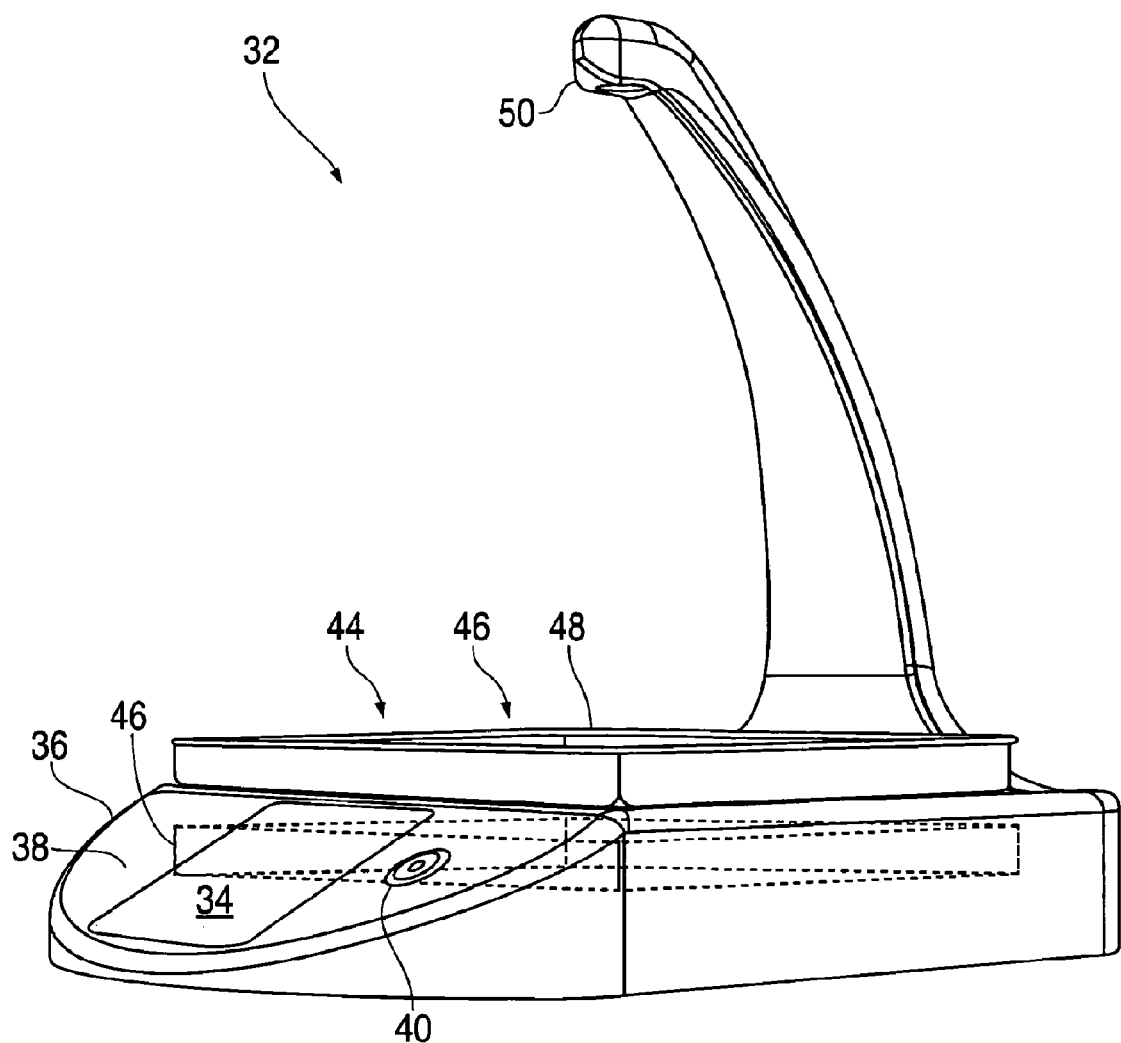
FIG. 2 is a perspective view of a counter and/or prescription verification device according to another example embodiment.

FIG. 2 shows another example embodiment of a counter 32. This example embodiment differs from the example embodiment of FIG. 1 in having an operator interface cluster 34 integrated into a base 36 on a sloped face 38 thereof, while a power switch 40 is located adjacent to the operator interface cluster 34. Electronic components for controlling the counter 32 are located within the base 36, beneath a stage 44 and an illuminator 46, rather than in a housing 24 integrated in part into the neck 18 as shown in FIG. 1. As shown in FIG. 2, a user-removable tray 48, which may be washable, sterilizable, and/or disposable, and which is substantially transparent to such portion of the electromagnetic spectrum as is used for illumination over at least a floor area thereof is illustrated as an example of a container that may be used to sit on the stage 44 to permit counting of pills (e.g., medication unit) disposed therein. The tray 48 may be smaller in extent than the illuminator 46 in at least some embodiments, which may tend to prevent units from resting thereon without being detectable. The tray 48 may be self-aligning in some embodiments, such as by fitting into a similarly-sized recess in the surface of the stage 44, by having alignment fittings in the tray 48 and stage 44 that establish an aligned position for the tray 48 on the stage 44, or by having another alignment provision. A tray similar to that shown in FIG. 2 may be suitable for use with embodiments such as those of FIG. 1 above, and other alternative embodiments as well. The counter 32, like the counter 10 of FIG. 1, is in the form of a single, unitized apparatus including, in this example embodiment, an imager head 50, the stage 44 enclosing the illuminator 46, a controller contained within the base 36, and the operator interface 34. The stage 44, illuminated from below by the illuminator 46, constitutes a background field for units placed on the stage 44, allowing the imager head 50 to be limited in its field of view to the area so illuminated.

Figure 3:
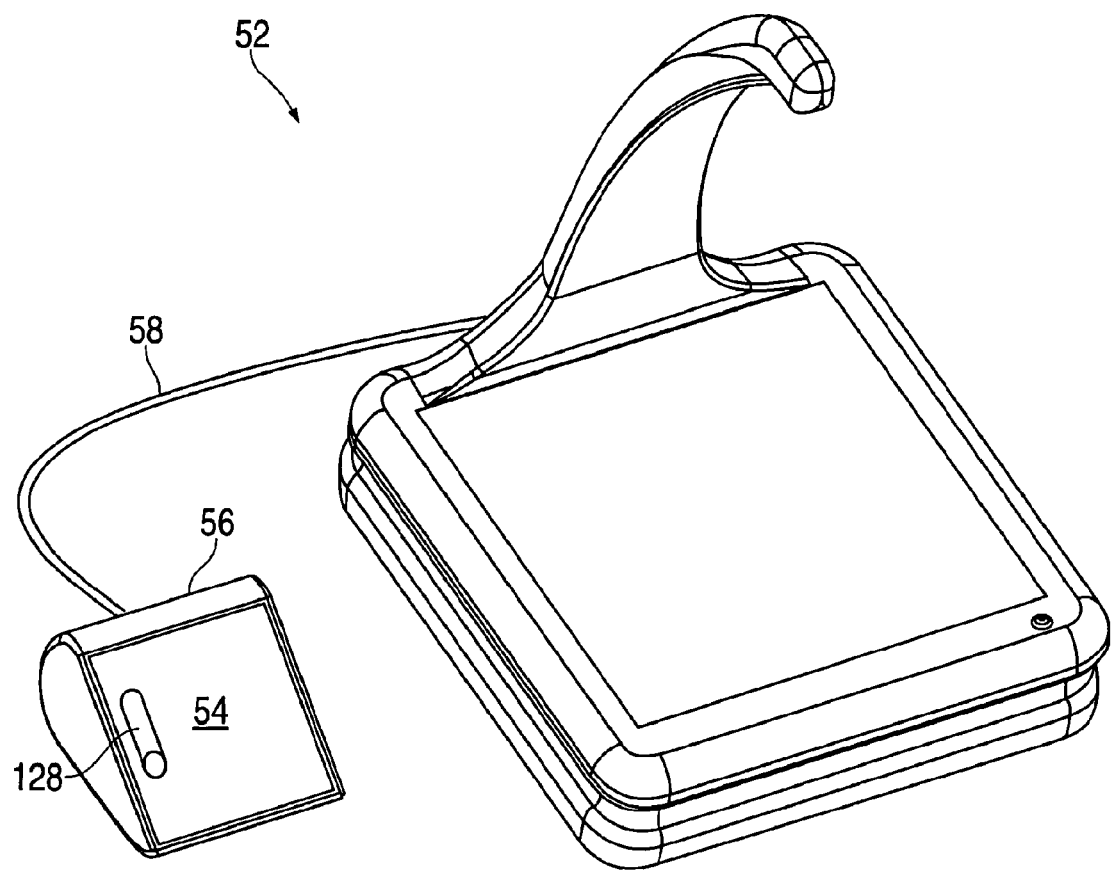
FIG. 3 is a perspective view of a counter and/or prescription verification device according to another example embodiment.

FIG. 3 shows another alternative embodiment in which a counter 52, substantially similar to the counters 10 of FIGS. 1 and 32 of FIG. 2. In the example of FIG. 3, an operator interface 54 is provided remotely by being located on a pendant 56 connected to the counter 52 by a cable 58. This arrangement, or a similar one wherein the pendant 56 is connected using a wireless link and may be separately powered, may be used in lieu of a more fully integrated apparatus in some applications. An orientation sensor 128 or selector may be provided, and may have the form, for example, of a tilt switch or absolute accelerometer embedded within the pendant 56, or may consist of a setup option for the processor. A display orientation provision based on such a selector or sensor may be used in some embodiments to rotate the display image for some pendant 56 orientations, such as converting from sitting on a table with the cable 58 behind to hanging on a wall hook with the cable 58 below.

Figure 4:
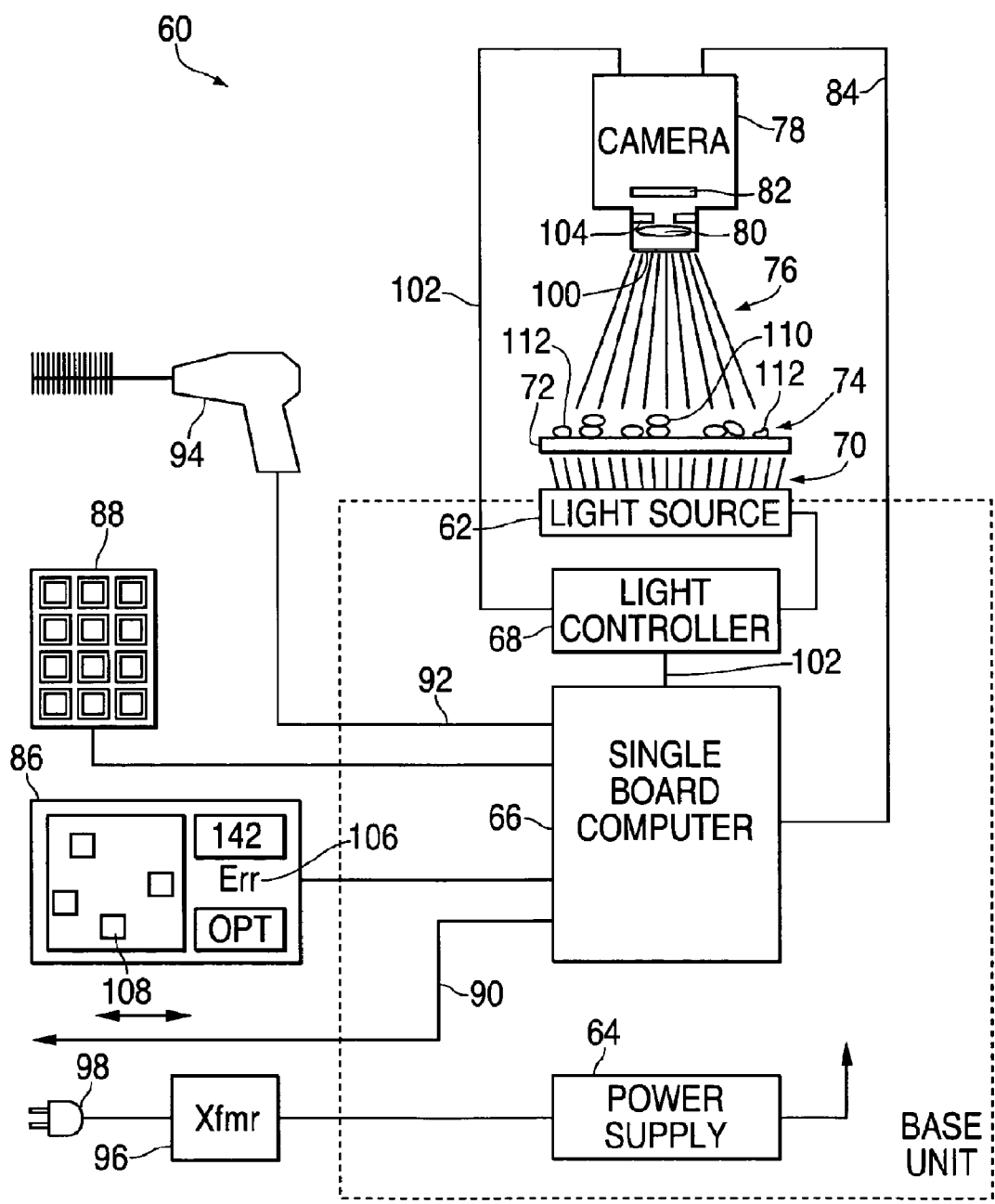
FIG. 4 is a block diagram consistent with a method according to an example embodiment.

FIG. 4 shows a counter 60, in block diagram form, having some of the functional elements indicated in the foregoing pictorial figures. The counter 60, may take the form of a single, substantially unitized apparatus, or may have some distributed components. As shown in FIG. 4, an illumination source (e.g., light source 62) powered from a power supply 64 with timing controlled from a processor module 66 may be provided. In some embodiments, the light source 62 may include a discretely identifiable illumination source power control module 68 that emits radiation 70, such as infrared light, that passes through a stage 72 and is blocked in part by subject units 74 (e.g., pills). A portion of the unblocked radiation 76 impinges on a camera 78, functioning as an image acquisition component, whereof a focusing mechanism 80 such as a pinhole or a lens may be used to place an image in the form of silhouettes of the units 74 on a detector 82, functioning as a machine vision transducer. The detector 82 couples the image in a transferable format such as a digital data stream to the processor module 66. The image is coupled via a power and communication link 84 such as a power-carrying electrical data signal cable or a combined power cable and fiber optic link in the embodiment shown. The processor module 66 further interprets the camera 78 image to generate a count of units 74 at periodic intervals. This count may be presented on a display component 86, and may be updated at a rate determined by a control routine stored within the processor module 66 or determined by input from a user, for example.

As described above, the camera 78 may simply detect a plurality of units 74 based on detecting the corresponding silhouettes of each of the units 74. As such, the camera 78 could be a relatively simple device with low resolution. However, in some example embodiments, the camera 78 may be further configured to capture a color image of the units 74. Features of the units 74 from the color image may then be compared to known features of the medication associated with a prescription being filled with the units 74 in order to attempt to verify that the units 74 correspond to the medication associated with the prescription. In other words, the camera 78 may be configured to generate a first image used to count the number of the units 74, and a second image (e.g., a color image) that is used to confirm or verify that the units 74 are the correct medication for the prescription. Thus, for example, the same camera (e.g., camera 78) may be used to take a color image and another image that need not necessarily be a color image. However, in some embodiments, two separate cameras may be provided, or the camera 78 itself may include two cameras.

In some embodiments, the camera 78 may include a flash or other lighting device to illuminate the units 74 from above to facilitate capturing the color image. However, any lighting device located substantially above the stage 72 on which the units 74 sit may be employed for these purposes. As such, regardless of whether one or two cameras are used for capturing image data, some embodiments may employ at least two light sources including light source 62 disposed below the units 74 for generating an image for counting, and another light source disposed substantially on an opposite side of the units 74 relative to the light source 62 for use in generating the color image. However, it should also be appreciated that some example embodiments may employ counting using the color image itself, or may not necessarily count the units 74 at all.

In some example embodiments, the counter 60 may include provision for local control input using a keypad 88. The keypad 88 may, in some example embodiments, have the form of a touchpad overlay, that is, an array of substantially transparent pressure transducers or a functionally equivalent device, providing output usable in place of pushbutton switch contacts, with the touchpad superimposed on the display component 86. Functions in some embodiments may also include one or more external communication links 90, whereby, for example, the counter 60 may operate a system or the system may operate the counter 60, as appropriate for an application. Such relationships are commonly described as master and slave; as appropriate, the counter 60 may selectably perform either master or slave functions or may be limited to one or the other.

In some example embodiments, another included interface 92 may support an optical reading device, such as a barcode scanner 94. Power for operating the counter 60 may be self-contained, using some combination of replaceable, rechargeable, and/or solar batteries included in the power supply function 64, may be externally powered using direct or indirect (such as from an external transformer 96) feed from a premises wiring plug 98, or may be otherwise energized, as selected for a particular use.

The light source 62 may, in some embodiments, provide electromagnetic energy in the form of infrared light at low average intensity and with a time-controlled, low duty cycle emission envelope. Where so implemented, the radiative intensity can be "strobed," that is, pulses of light can be emitted having a selected rate, duration, and emission intensity envelope. In strobed configurations, overall emission may be substantially lower than would be the case were the light source 62 operated continuously at an emission level compatible with the camera 78. This may, in some embodiments, allow a high enough illumination level for efficient operation of the camera 78, while lowering the net power radiated and/or conducted downward into any electronic devices housed below the light source 62. This can in turn reduce component stress, extend component life, reduce overall power consumption and power supply size and weight, and/or reduce tendencies for susceptible components to drift in value with temperature. Strobe capability may further allow operation without a cooling/air distribution fan in some embodiments.

In some embodiments, a planar array of infrared light emitting diode (LED) devices, substantially matched for uniformity of emission intensity and wavelength, and affixed below the stage 72, may be used to establish a diffuse illumination source. In other embodiments, a single, possibly higher intensity device, effectively a point source, the emission from which is distributed and directed by a lens, a focusing reflector, or a combination of such accessories, for example, may be used as the illumination source.

Light having a wavelength outside the infrared portion of the spectrum may be used in some example embodiments. Illumination may likewise be of multiple wavelengths, such as white light. One or more downward-directed illumination sources, such as, for example, ambient room light or a second light source at camera 78 level (shown also as source 116 and camera 118 in FIG. 5), may permit one or more attributes of the units 74 in addition to quantity and/or shape to be detected, such as color, size, transparency, imprint symbols, surface features/markings, and the like. In embodiments having a plurality of light sources and/or a source emitting a plurality of colors, reflected light in addition to or in place of silhouette illumination may be detected. Such capability may in some embodiments permit or enhance detection of flawed or incorrect units in a sample, for example. Alternatively or additionally, detection of features or attributes of the units 74 using downward-directed illumination may enable the units 74 to be classified or otherwise compared to known units that match the prescription being filled. The camera 78 of FIG. 4 may acquire a reference brightness level when the stage 72 is empty, then use the reference level to establish contrast levels during counting and/or classification.

Illumination using energy other than infrared and visible light may be used in some embodiments. Within the electromagnetic (EM) spectrum, microwave radiation (i.e., EM waves longer than infrared) may provide adequate resolution in some embodiments, while ultraviolet light (UV, EM above visible) or x-rays may be usable in other embodiments. Acoustical energy, such as ultrasonic emission, can have wave dimensions and power levels permitting acquisition of an image of a stage whereon a number of countable units are placed, with sufficiently high resolution and image refresh rate to meet system needs. Still other imaging methods and media may likewise be applicable in some embodiments.

Contrast between the appearance of the surface of the stage 72 and of the units 74 being counted may be further enhanced, particularly in a high ambient light level or broad-spectrum light environment, by positioning one or more filters 100 having properties suitable for limiting light impinging on the detector 82 to spectral elements of interest. For an infrared source illuminating a detector that is insensitive and thus self-filtering for spectral elements longer in wavelength than the far infrared, an infrared low pass filter may be used, while for embodiments wherein multiple spectral elements are to be detected, combinations of low pass and/or band blocking (notch) filters may be used. It is to be understood that a single filter 100 combining multiple notch filters and bandpass or lowpass filters may be used in some embodiments.

In embodiments using strobing, synchronization by a sync signal line 102 may be directed from a relevant circuit element such as the processor 66 or the power control module 68 to the camera 78. Applying the sync signal to the camera 78 allows image acquisition to be synchronized to the availability of light from the light source 62. The strobe function can reduce energy flux and gradient into the units being counted, thereby impeding degradation for some heat-sensitive, light-sensitive, or short-life medications or packaging configurations.

Figure 5:
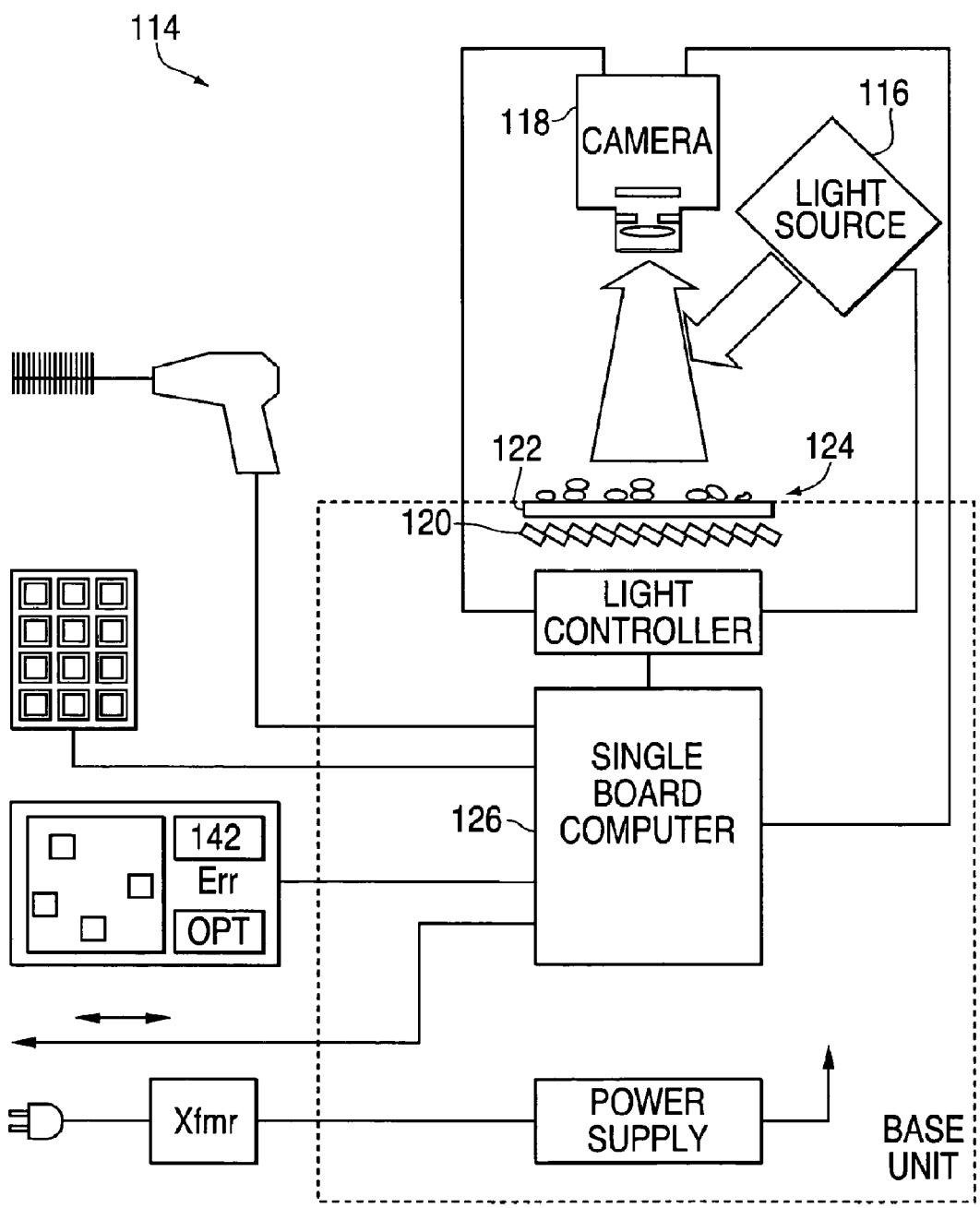
FIG. 5 is a block diagram of an alternative example embodiment.

FIG. 5 is an example of another example embodiment of a counter 114, wherein a light source 116 is positioned substantially at the level of the camera 118. The light source 116 may be diffuse, that is, may have largely uniform and low energy density emission over a relatively broad surface, or may approximate a point source, that is, may emit with comparatively high energy density from a small spot. Each such configuration, as well as intermediate forms such as multiple discrete spot sources, may be superior in conjunction with particular imaging methods.

For some embodiments, a passive reflector 120 beneath stage 122, which may be focused, can be used to reflect light from the light source 116 back to the camera 118, with deflection or diffusion of the light by the units 124 providing contrast. The reflector 120 in FIG. 5 is a collapsed type, such as a metalized negative Fresnel lens; other configurations are feasible as well. The size shown for the reflective components of the reflector 120 is larger in FIG. 5 than in some embodiments, with the understanding that finer scale reflective components can more readily establish a low-profile, accurately focused mirror, while components comparable in scale to the units being counted may be preferable for other embodiments. For still other embodiments, a stage or substage surface that largely absorbs or deflects the wavelength of the light source 116 may be used, so that the units 124 are seen by the camera 118 as brightly lit against a relatively dark background. The last embodiments could require an adaptation of the processor 126 algorithm to account for discrete specular reflections from gel capsules, coated pills, and other shiny unit surfaces, for example. Similarly, variations in reflectivity of subject units may require added camera bit depth or processor algorithmic complexity in some such embodiments. Embodiments using reflectors 120 beneath the stage 122 could be unsuitable for counting some types of reflective units unless the position and other attributes of the illumination source were arranged to accommodate such uses, such as by offsetting the light source 116 with respect to the central axis of the camera 118 field of view.

In still other embodiments, comparable resolution and speed may be achieved using a narrow, directable spot of light, such as a laser beam within the light source 116, directed over an area using a Micro Electro Mechanical System (MEMS) or another beam steering system. In such an embodiment, the beam is scanned over the stage, and the scan result is detected by a "camera" 118 that can be as simple as an unfocused single-element photodetector. Such an embodiment may use silhouette, reflection, or combined imaging, and may use a plurality of light sources of different wavelengths. The analytical algorithm for evaluating an image so acquired, discussed below, may also be adapted, such as by performing a low-resolution scan with the beam to find unit candidates, then edge tracing or rescanning at higher resolution to evaluate areas of interest. The process may further vary spot size.

In some embodiments, an areal counting function may be executed repeatedly at selected intervals, with count results on the display 86 of FIG. 4 then updated, for example after completion of each count. For sufficiently rapid count intervals, such as multiple times per second, the update rate may appear to a user to be essentially continuous. As an operational consideration, such a process may allow a dispensing agent to pour out units onto the tray 54 of FIG. 2, for example, until an approximately correct count is seen on the display 86 of FIG. 4. The agent can then verify that no piles obscuring observation are present on the tray 54, and can redistribute the units if necessary, with the results presented effectively instantaneously at each step.

In some embodiments, in addition to providing a count of discretely identifiable units interrupting illumination over several consecutive scan lines at a broadly uniform position with reference to a first end of the scan lines, a processor 66 may provide an inspection function. That is, the processor 66 may be configured to anticipate the approximate areal coverage or "blob size" of the units being counted, and to determine for each discretely identifiable unit whether the size generally corresponds to that expected for such a unit, in consideration of a range of orientations of the unit. Thus, for example, where unit size is too small to be consistent with any anticipated orientation for that unit, the unit may be tagged as possibly chipped or a fragment. Similarly, where a unit occupies a large enough region but shows a shape that is nonuniform, exceeds a stipulated range of rates of curvature, or otherwise exceeds geometric model limits, the unit may be tagged as possibly defective. Such information may be presented on the display 86 of FIG. 4, variously in text form 106 or as a graphical image 108 showing the general location of a suspected fragment 112. Fragments below a stipulated size may be ignored in some embodiments. Furthermore, in some embodiments, the size may be used as a component of determining whether the units are the correct units for the prescription being filled as described in greater detail below.

Compound element images may be identified as multiple discrete units through application of geometric pattern matching functions. Where predefined or other geometric patterns can be detected within a compound element image, the patterns can be classed as units within the image. The patterns defined by these units may be, in effect, subtracted from the image, leaving the areas obscured by the patterns indeterminate, i.e., classed as neither illuminated nor part of the silhouette image. The remaining image may then have the pattern matching function further applied, and other patterns may in turn be identified. Such an iterative process may in some embodiments permit compound images to be partitioned and counted with acceptable accuracy, and may further allow identification of broken pieces of units. The process may further identify and tag extraneous items—that is, items not having geometric patterns corresponding to units or combinations of units—with these omitted from a count. This process may be termed discrimination between patterns.

In some embodiments, the processor 66 may identify touching or overlapping units, allowing counting of units within multi-unit groups in some configurations and directing an agent to scatter such groups where likelihood of accurate counting is unacceptably low. It will be understood that a limit on such capability may occur where units such as flat-faced pills-squat cylinders—are stacked 110 substantially perpendicularly to the local view axis of the camera 78, as shown in FIG. 4. Such configurations may reduce the efficiency of the counting machine despite use of procedures outlined above. Additional procedures such as the one discussed below may restore efficiency.

In some embodiments, the processor 66 acquires a unit count over multiple sample cycles, during which interval the agent may add units to the stage 72. The processor 66 compares unit counts in successive sample cycles, with successive counts typically increasing in value. Where a final count target is known, the agent may need to add or remove units after a stable count is established. Under some conditions, a count may be observed to decrease anomalously, which may result from stacking 110. A processor 66 detecting such a condition may present a message to the agent directing that the units be spread, and may further indicate one or more regions on the stage 72 as appropriate.

Figure 6:
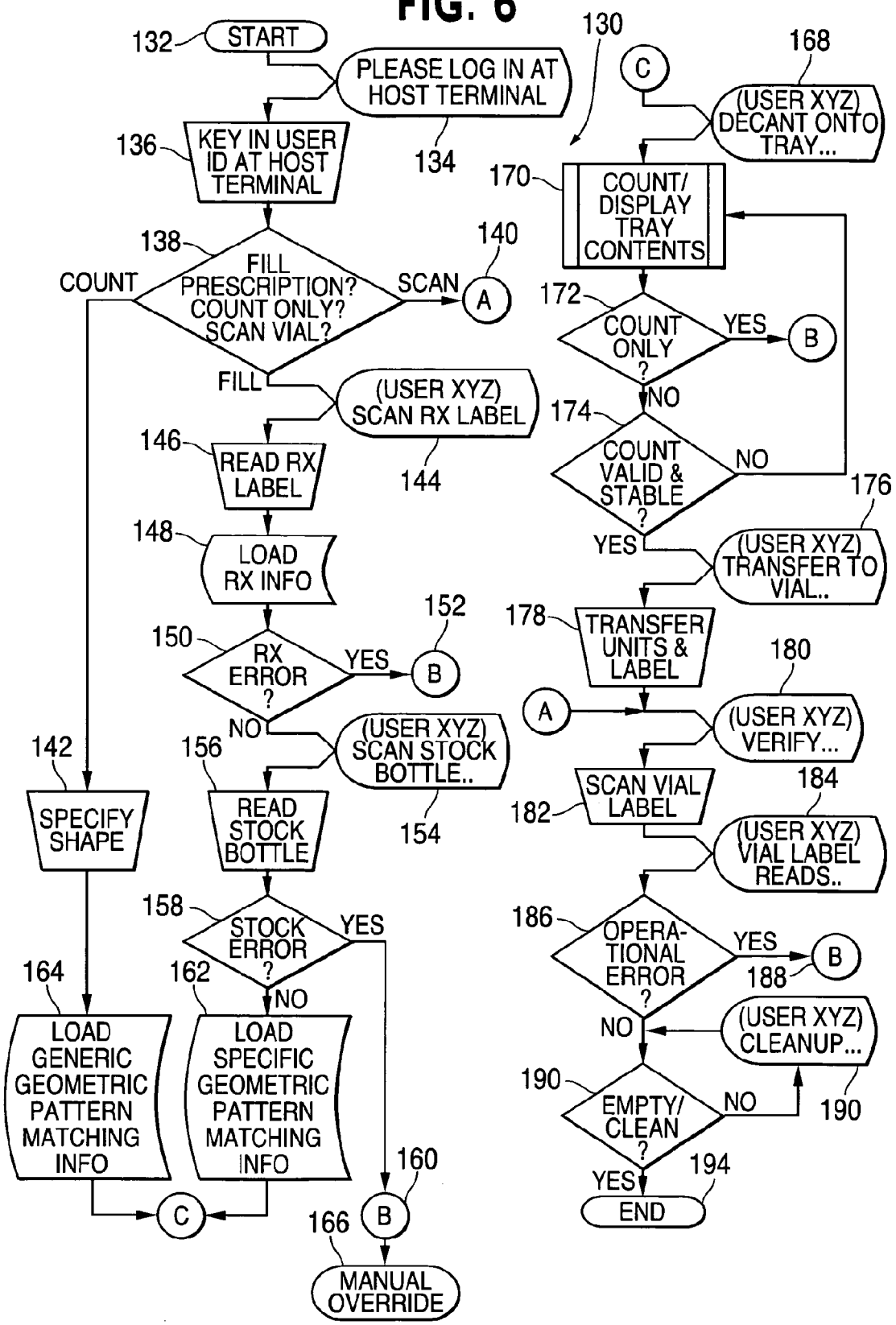
FIG. 6 is a flowchart indicating a procedure followed by a counter and/or prescription verification device operating according to an example embodiment.

FIG. 6 shows default overall signal flow according to one example embodiment of the invention. After initialization 132, an agent is prompted 134 to perform a login function 136. Note that in a standalone system configuration or a configuration wherein the counter in use is the master, the term "host terminal" may apply to the counter itself. For such applications, the counter can support digital data entry, such as for login, as a function of the display 86 and of the touch-screen or keypad 88 of FIG. 4. For other embodiments, a host separate from the counter may provide login confirmation input through the communication link 90 of FIG. 4.

Once an agent (here, USERXYZ) is recognized, task options 138 may include, in some embodiments, filling a prescription (Rx), performing a count on units not associated with a prescription, and scanning an existing prescription vial. Where the task is limited to scanning an existing vial, count processes are bypassed, and execution jumps 140 to a later node in the routine. Where the task is to count units, an indication of unit shape may be provided 142 by the agent to the counter 130. Where the unit shape is known, the agent can select the shape from a menu referencing a database, for example. Where the unit shape is not available from a resource, the shape can be specified for the task by defining a geometry in terms of curvature, diameter, and the like, defaulting to a nominal shape and size, or another method. In some embodiments, reference information regarding pill shapes may be stored (e.g., as .bmp files) in a database. When an unknown pill shape is encountered, the counter 60 may be configured to prompt the operator to place two pills on the tray (one flat and one on its side) to capture an image for recording in the database to learn and save the reference shape of the previously unknown pill shape.

Where the task is to fill a prescription, the counter can prompt the agent 144 to scan 146 a reference document such as a previously prepared prescription label. For some embodiments, a method for scanning may use the bar code scanner 94 of FIG. 4 to read a bar code printed on the label. In other embodiments, the scan process may involve keypad entry of a reference number, or may require entry of text such as prescriber's name, formulation, quantity, and the like, with a label being printed, as a response to the input, using a printer external to the counter.

After the prescription label information is acquired, associated information may be loaded 148 from a reference resource external to the counter, using, for example, the external communication link 90 in FIG. 4. However, in other embodiments, some or all of the associated information may be contained in a database internal to the counter 10. The loaded information may be evaluated for some classes of errors 150, such as an unauthorized or already-filled prescription, and, if defective 152, brought to the attention of the agent 160, 166. Where the information is proper, the counter can prompt the agent 154 to scan 156 a stock bottle (a bulk storage container for a prescription), using the method previously used 146 for the label. If the stock bottle is incorrect 158, the agent is directed to intervene 160, 166; if correct, geometric pattern information for the units may then be loaded from a database 162, where the database information is maintained within or external to the counter. At this point, the generic counting option and the prescription filling option paths from step 138 converge, with a geometric pattern not associated with a prescription loaded 164, and the procedure continuing to the count phase.

The agent is then directed 168 to decant the units into the tray, after which the count function loop described in FIG. 6 is invoked 170. If the procedure is only a count 172, then the loop may be limited to a single execution pass. If not, the loop may instead monitor the decanting process by repeatedly executing the counting process 170 until a valid count is achieved 174, discussed in detail below. To complete the procedure, the agent is directed 176 to transfer the counted units (and the label, if not previously done) to the final vial 178, then to verify 180 by rescanning the label 182, which is then displayed 184. If a mistake has occurred 186, the agent is directed 188 to intervene 160, 166; otherwise, the scan surface is examined for visible contamination 190 and the agent may be prompted to clean the scan surface 192, after which the procedure is finished 194.

Figure 7:
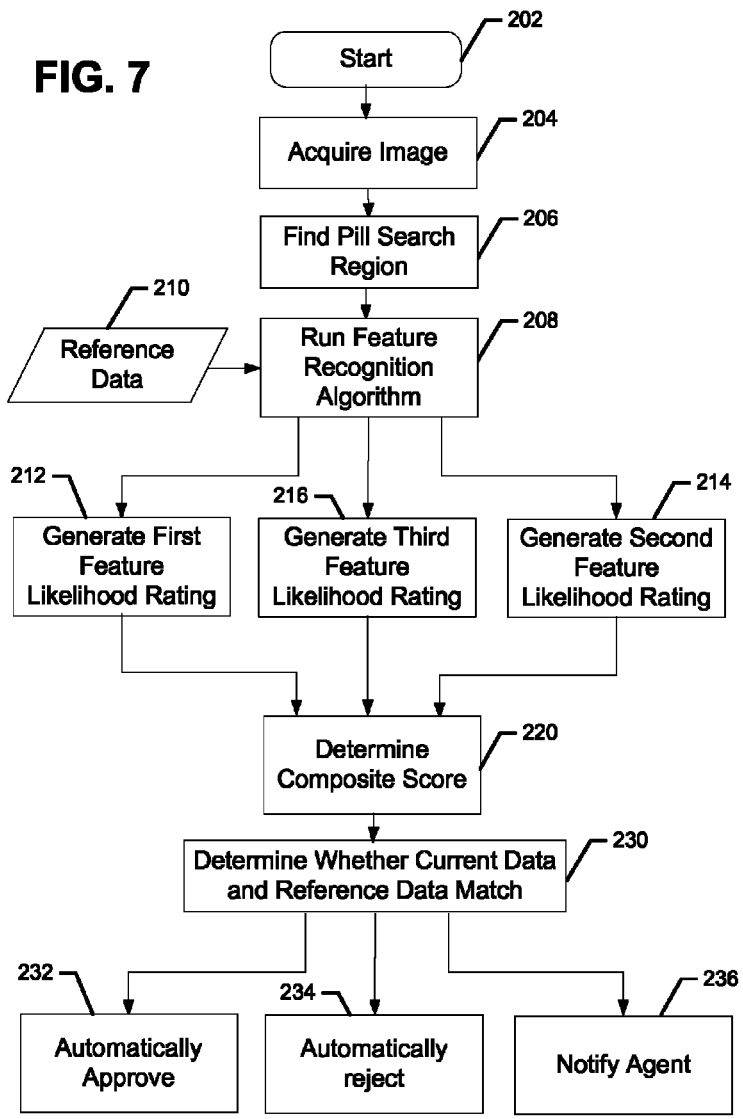
FIG. 7 is a flowchart indicating a prescription verification procedure according to an example embodiment.

FIG. 7 shows an example process 200 for verifying a prescription based on the content of a scannable tray. As indicated in the flowchart of FIG. 6, a stock bottle reading 156 or a specific or generic shape definition 142 allows geometric pattern matching information 162 or 164 to be applied to a counting task 170. As is further shown in FIG. 7, characteristics known about the medication to be dispensed in association with the prescription may be used to determine whether the medication units or pills on the scannable tray are the correct units to verify the accuracy, not only of the pill count, but of the type of pills being dispensed. In this regard, the process 200 may utilize an image (e.g., a color image) of the contents of the tray to compare features of the pills on the tray to known features of the pills that are to be dispensed for the prescription being filled.

As shown in FIG. 7, a classification function may be initialized at operation 202 and a tray image may be acquired at operation 204 for the routine. The tray image may be a color image of the contents of the tray disposed at a stage of the counter. In some cases, a pill search region may be found at operation 206. The pill search region of one example embodiment may isolate a single pill. However, in other embodiments, multiple pills may be isolated in the search region to provide different perspective views of the pills for comparison to corresponding perspective views of reference data. A feature recognition algorithm may then be run at operation 208 based on comparing known features of reference data 210 for the medication units or pills associated with the prescription to the features of the pill (or pills) in the search region.

The features compared may include, for example, color, size, shape, pill markings (e.g., printed material on the pill, surface features, embossed markings or symbols, and/or the like) or other features that may be used to identify pills. In an example embodiment, the reference data 210 may be acquired via image capture of sample pills corresponding to each of a plurality of medications, where the images captured are captured using a same or similar model of counter as the one employing the process 200. Accordingly, the reference data 210 may include images of the pills taken with substantially the same camera resolution as the images acquired at operation 204. Moreover, the reference data 210 includes images of pills in the same state and/or position as those that will be analyzed (i.e., in the tray on the stage). Since the pills being analyzed are on a similar tray and positioned substantially flat upon the tray like the pills in the reference data 210, relatively consistent perspective may be maintained to improve correlation capabilities. In this regard, the pills have a known position (e.g., on a tray for counting prior to disposal into a pill bottle) and relatively large probability of having a known orientation in the known position (e.g., lying flat, with a largest profile of the pill oriented upward). The pill images compared can therefore be expected to inherently account for any differences in scale, perspective, camera resolution, lighting or other factors that may impact the images. To the contrary, if a commonly available on-line database is used to provide reference data, or if other generic images of reference pills are used, camera resolution differences may cause some high resolution images to fail to match to corresponding low resolution images. Similarly, pills imaged within a pill bottle in a random orientation may not match with reference pill images in a different orientation. Other differences may also contribute to failure to be able to classify medications properly.

In some embodiments, the reference data 210 may be gathered on the same machine that is used to employ process 200. However, in other embodiments, the reference data 210 may be locally or remotely stored based on images gathered by a different machine that is either of the same or similar model as the machine that employs the process 200. The reference data 210 may include a plurality of reference images, or data descriptive of features extracted from reference images, that can be compared to images captured by the device employing the process 200 in order to verify that the pills currently being analyzed match the pills that are known to correlate to the current prescription being filled. Thus, for example, after the prescription is identified (e.g., by barcode scanning or other methods), the corresponding reference data 210 may be obtained from a database or memory device (locally or remotely located), and the reference data 210 may be compared to the current images or to features extracted from the current images.

In an example embodiment, the feature recognition algorithm may be constructed to analyze each of one or more features individually to determine a likelihood rating for each respective one of the features analyzed. For example, as shown in FIG. 7, a first feature likelihood rating may be generated at operation 212, a second feature likelihood rating may be generated at operation 214, and a third feature likelihood rating may be generated at operation 216. Additional operations for corresponding additional features may also be performed as appropriate given the features over which analysis is performed. The first, second, and third features that are analyzed for the likelihood ratings of operations 212, 214 and 216 (and also any additional features) may correspond to any of size, shape, color, and pill markings in some examples.

Features of the reference data 210, for the current prescription, may be compared to the corresponding features in the image captured at operation 204. As an example, color features of the pill or pills in the image captured at operation 204 may be analyzed relative to corresponding color features of the pills that correspond to the prescription being filled. The color features may include sub-features such as wavelength, intensity, opacity, and or the like. Of note, since contextual differences can sometimes cause objects having the same objective color to appear differently, the fact that example embodiments use images captured with a similar or same machine may tend to eliminate contextual differences and therefore result in more reliable correlations when color rating is performed than those that could otherwise be achieved by attempting to correlate images taken with different hardware or under different conditions.

Other features such as size, shape and pill markings may also be compared between reference data 210 and current data (e.g., data in the image captured at operation 204) to determine corresponding likelihood ratings. In some embodiments, the markings may be compared by converting the markings into text that may then be compared to text that is stored in the database for known drugs. Other features may also be broken into sub-features in some cases. In any case, each sub-feature or feature may receive a correlation score as the likelihood rating. Depending on the scoring paradigm employed, a high or low score may indicate a high degree of correlation between the images compared. In some embodiments, the scores may be rated as having a high, medium or low degree of likelihood of a match, or may simply receive a raw score. After each feature has been scored, a composite score may be determined at operation 220. The composite score may then be compared to various thresholds to determine the overall likelihood of a match. In some cases, only the composite score may be used for determining the overall likelihood of a match. However, in other cases, having a score that is below a certain threshold in any one feature category may disqualify the pill from receiving an overall matching score, regardless of the scores in other categories. For example, if the size, shape and markings on the pill from the current data match very closely (and thus have high likelihood ratings for each respective feature) with the size, shape and markings on the corresponding pill from the reference data 210, but the color is clearly and distinctly the wrong color as indicated by a very poor likelihood rating for color, the pill may be disqualified from matching even if the composite score may not be low enough to otherwise disqualify the pill. As such, the individual rating of each feature may provide for improved differentiation among pills and therefore increase the accuracy of verifications made by example embodiments.

Based on a likelihood score (e.g., based on the individual feature scores and/or the composite likelihood score), a determination may be made as to whether the reference data 210 and the current data match (e.g., based on the likelihood score or rating relative to a predetermined or threshold level) at operation 230. A determination may also or alternatively be made based on a result of comparing likelihood scores of presented pills to all known pills in the database and confirming whether a prescribed pill has the highest calculated likelihood. If another pill has a higher likelihood score, the operator may be alerted. In some embodiments, scores above a certain threshold level without disqualifying sub-feature or feature scores may be automatically approved at operation 232 and the operator may be signaled to indicate that the prescription may be filled. Scores below a certain threshold level or with disqualifying sub-feature or feature scores may be automatically rejected at operation 234 and the operator may receive a warning that the prescription should not be filled. Scores in between the thresholds defined at operations 232 and 234 may be indicated to the operator so that the agent may visually inspect the pills to determine if there is a match and proceed with filling the prescription at operation 236.

Referring again to FIG. 4, in some embodiments, the image acquisition process provides a timing signal on a signal line 102 both to activate the illumination source 62 and to initialize the camera 78 to perform a raster scan over the stage 72. Each picture element (pixel) in the field of the camera 78 is converted from a light intensity level to an electrical signal level by the camera 78. The signals, which may be analog in form, are then digitized, either intrinsically, internally to the camera 78, or within the processor 66. In some embodiments, multiple colors or shades of gray may be acquired, using one or more light sources 62. Images then utilize multiple bits per pixel: two bits to represent four discrete levels or colors, four bits to represent sixteen, and so forth to provide enhanced capabilities with respect to detecting features of the pills to verify whether the pills currently imaged correspond to known data regarding the pills for which the corresponding prescription was written.

In some embodiments, the process 200 of FIG. 7 may be run subsequent to (or prior to) execution of a routine used to count the pills that may be similar to the routine described in connection with the example of FIG. 6. However, in other cases, the count routine and the verification process may be combined into a single process flow. The presentation of all of the pills associated with a count operation in the tray on which the image data is captured allows for both counting and pill verification operations to be performed by a single device. After counting and verification are performed, the pills may be deposited into a pill bottle to fill the corresponding prescription and the pill bottle may be issued to a patient to whom the medication has been prescribed.

Figure 8:
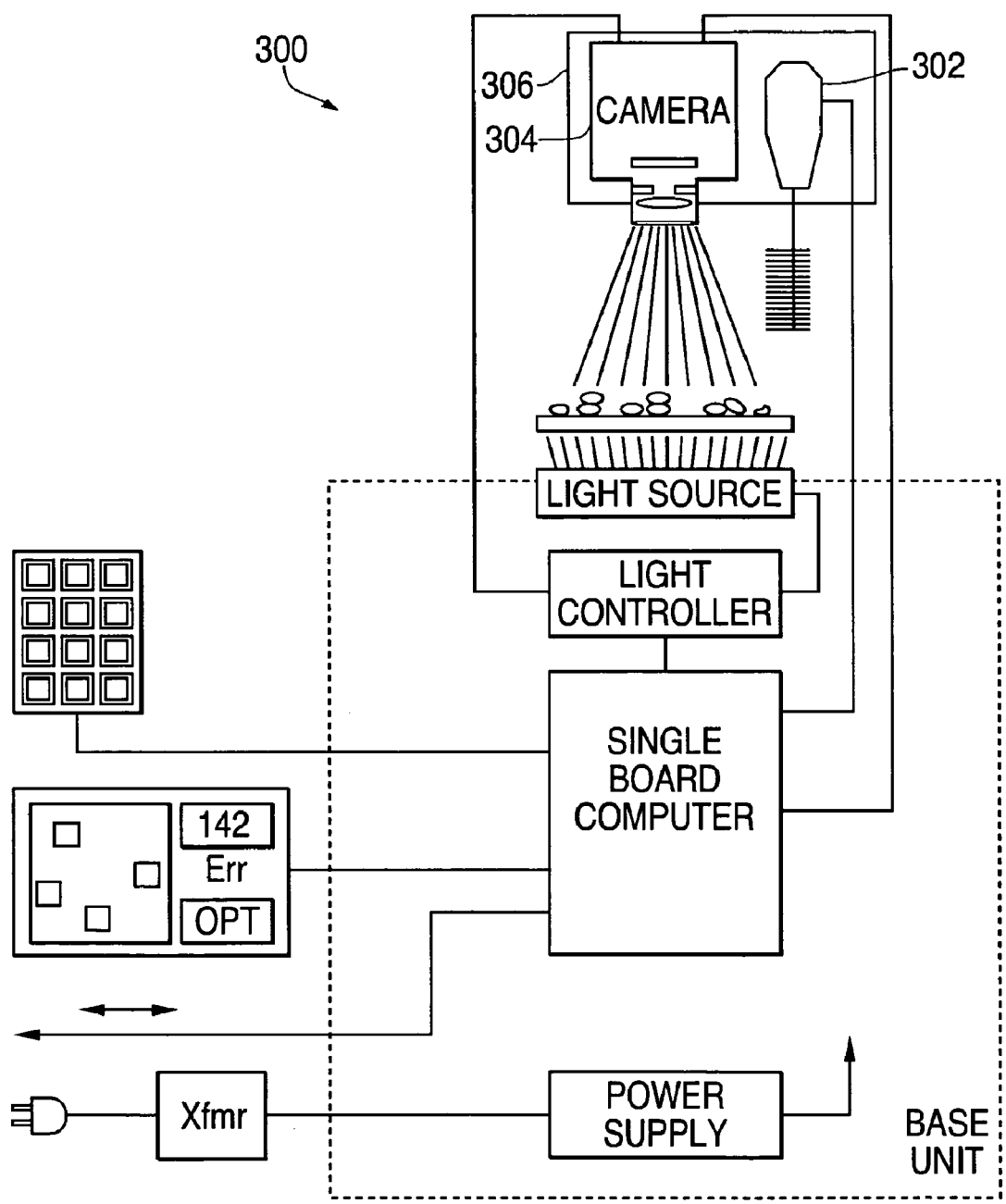
FIG. 8 is an additional alternative example embodiment in block diagram form.

FIG. 8 shows the block diagram of FIG. 4, further adapted such that an apparatus 300 of the pictured example includes a data acquisition device 302. The data acquisition device 302 may be generally similar to the bar code scanner 94 shown in FIG. 4 and can be integrated into the head 304 containing the camera 306 in some embodiments. In some example embodiments, the data acquisition device 302 may provide one- or two-dimensional bar code scanning by moving a self-supplied visible light source, such as a steerable laser beam, over a field such as an agent identification card or an encoded reference number on a stock bottle. The sequence of light intensities reflected from the field can then be sensed and interpreted as a string of data elements that encode selected information. The information may include that described above in discussion regarding FIGS. 4-7, such as prescriber and product codes, as well as security information. In other embodiments, the light source may be infrared, for example, or the scanning process may use a radio or magnetically coupled signal to acquire data. In some embodiments, the scan function may be performed by components also used for image acquisition.

Figure 9:
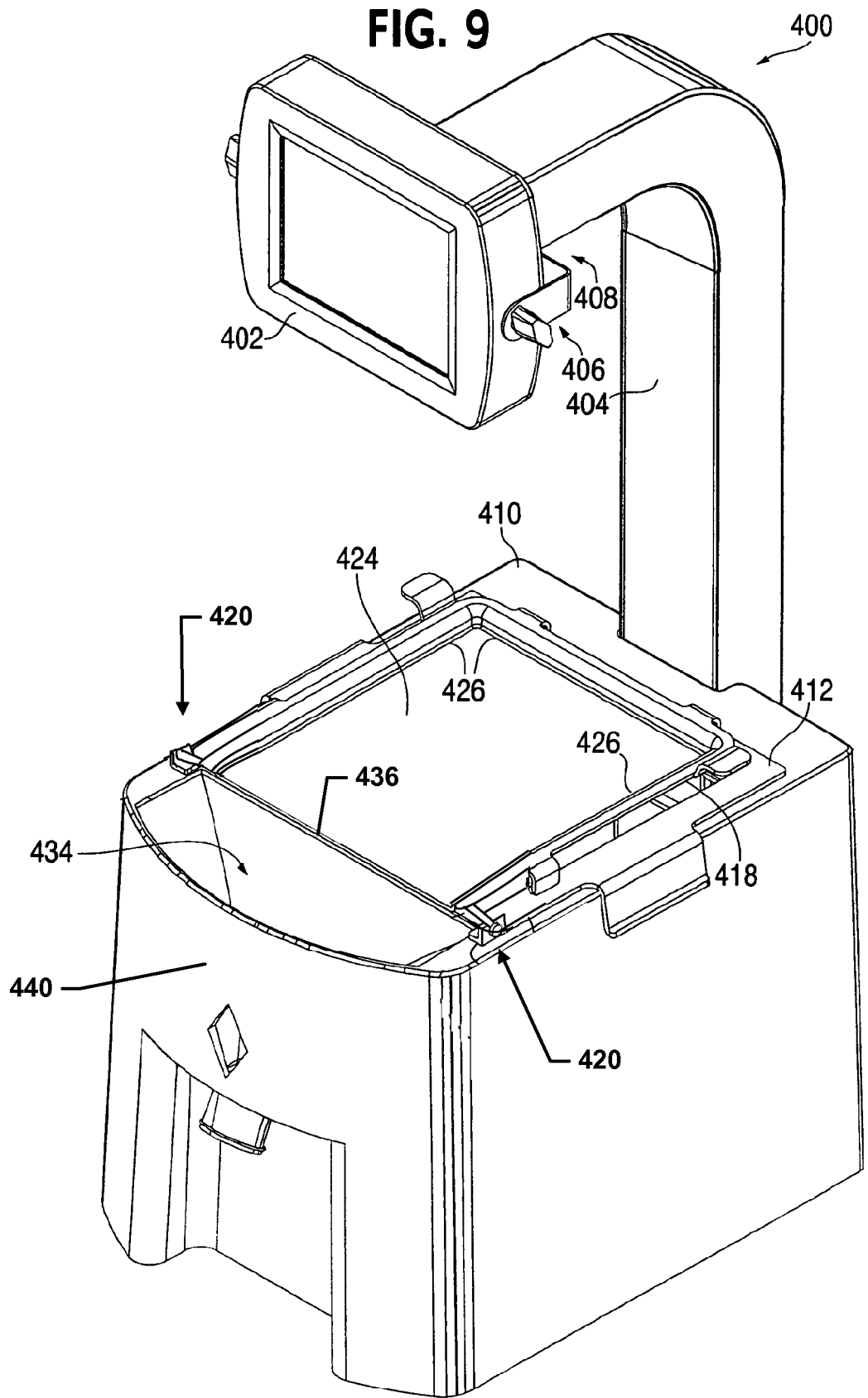
FIG. 9 is a perspective view of an additional alternative according to another example embodiment.
Figure 10:
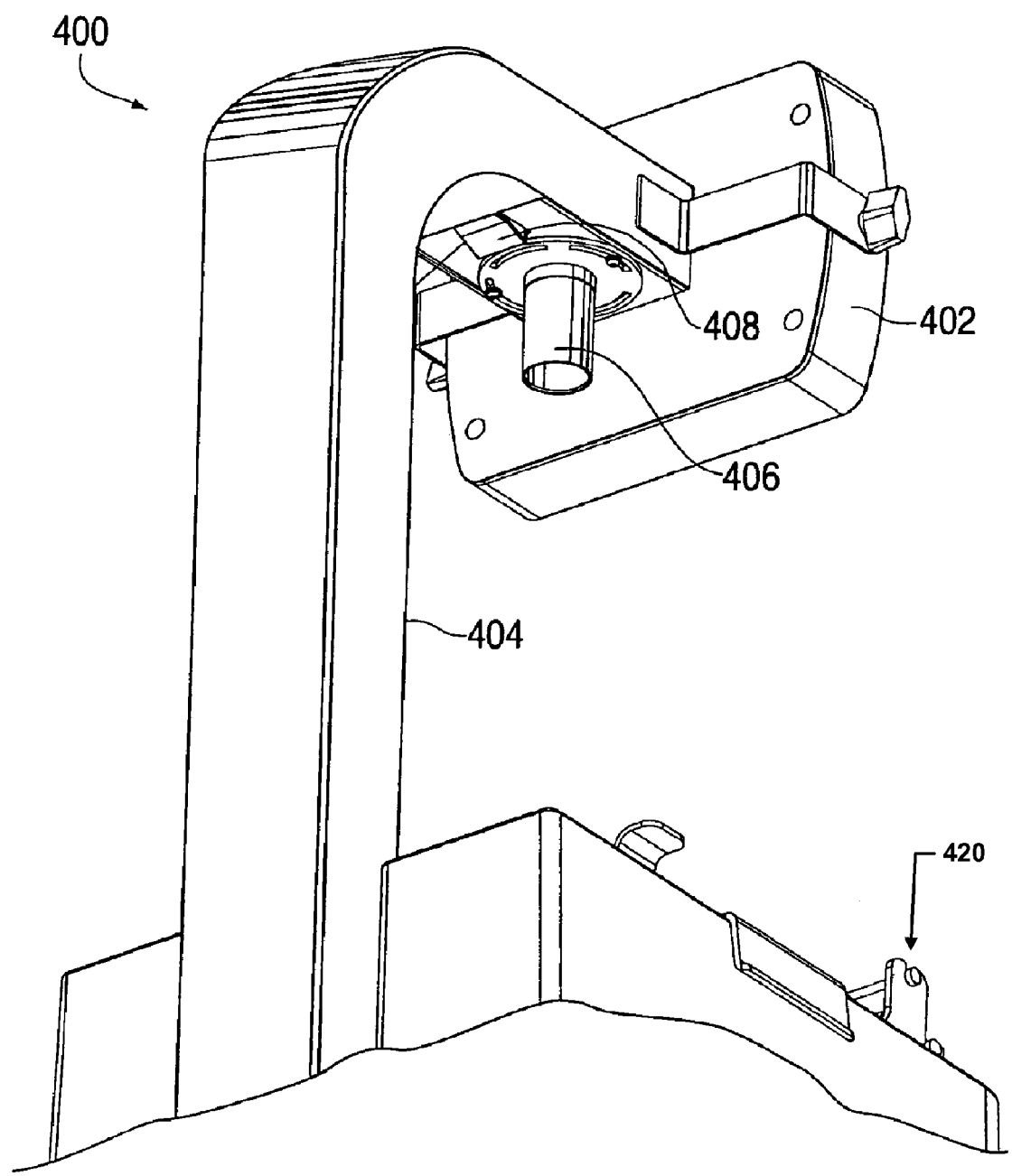
FIG. 10 is an additional view of the example embodiment shown in FIG. 9.

FIG. 9 shows a perspective view of still another example embodiment of a counter 400. In this embodiment, a display/user interface 402 is positioned at the top front of a principal support arm 404. A camera 406 and a scanner 408, visible in FIG. 10, are located on the arm 404 behind the display 402. A base 410 may have an adapter 412 affixed thereto. The adapter 412 may be configured to accommodate the tray 418 and a hinge assembly 420 that may permit the tray 418 to pivot such that a portion of the tray 418 that is located proximate to the support arm 404 may be elevated while the opposite end pivots about the hinge assembly 420 to empty pills in the tray 418 into a guide chute 434. In an example embodiment, the tray 418 may include a front lip 436 that may be lower than other walls of the tray 418, but high enough to keep pills on the tray 418 until the tray 418 is pivoted in order to empty its contents into the guide chute 434. The front lip 436 may extend over a substantial portion or even an entirety of the edge of the tray 418 that is proximate to the guide chute 434.

In an example embodiment, the guide chute 434 may include a front panel 440 that may be transparent in some examples. By making the front panel 440 transparent, pills dumped from the tray 418 and into the guide chute 434 may be seen as they transit down the guide chute 434 to fill a pill bottle. Accordingly, the agent can easily see whether any pills are hung up or obstructed from completing their journey into the pill bottle after being dumped.

It is to be understood that the hinge embodiment presented in FIGS. 9-10 is one of many possible arrangements. For example, mating depressions and protrusions on the respective components can provide hinge function in lieu of identifiable hinge pins and pivots, or separate hinge pins can be used along with bearing fixing holes and/or attachment points in each part to provide hinge function. In other embodiments, multiple components can be molded as a unit from a material sufficiently resilient that the hinge functions can be realized using so-called self-hinges. That is, allowance for repeated bending of the material, such as at purpose-made locations, i.e., self-hinges, can enable the required range and ease of motion without recourse to multiple parts. Similarly, discrete components can be connected with resilient hinge material to accomplish comparable functionality. Selection of one or more of these arrangements or others that will occur to those proficient in the relevant arts may depend on the requirements of a specific embodiment.

The foregoing process may be compared to the process required for an unpivoted tray, as shown in FIG. 2, wherein the agent lifts the tray from the stage, tilts the tray to direct the units into a corner of the tray, then further directs the units into a receiver bottle. It is to be understood that a unit handling arrangement using a pivoted tray and an associated chute may be adaptable to the embodiments of FIGS. 1, 2, and 3.

Various features may be included in the inventive apparatus to augment security. The features may include, for example, control of software configuration modification, so that downloading an altered database of geometric data defining unit shape requires a password or other, more rigorous identification. Stock bottles may be provided with geometric data embedded in a bar code, so that no separate database is required, and the bottle and its contents are logically linked. Regarding technology choice between one-dimensional and two-dimensional bar codes, it is to be understood that the embedded geometry describing a specific unit may be more readily implemented in embodiments employing the longer sequences possible with two-dimensional bar codes.

Other features potentially desirable in some embodiments include a requirement for a long and/or encrypted agent badge code, embedment within the agent badge code of one or more biometrics such as a scan of relative finger length profile, a requirement that a password be changed periodically, or a combination of these and other security measures. It is to be understood that processor-based security functions associated with a counter may include procedures to acquire affirmative information, such as badge code decryption and confirmation, polling of individual subassemblies to acquire and examine condition reports, transmitting test codes and verifying responses, and the like. Thus, an indication that counter security status is good can be derived from an affirmative security test sequence that may be extensive in some embodiments.

Further, negative events may negate a security good indication. For example, a loss of a power good signal from a power supply may generate a processor interrupt for system shutdown without data loss, which can be usable in embodiments where prior system state is needed during restart, for example. Similarly, specific security related or operational negative events may be detected, such as removal of a closure seal on the counter, timeout of a watchdog counter, overtemperature detection from a thermal sensor having go/no go state switching, and the like. Identification of a recognized agent may be viewed as an affirmative security procedure enabling operation, while touching a "standby" button on a touchscreen or absence of agent input, including change in count or position of units on the stage for a stipulated period, may be viewed as a negative security event initiating disablement of operation. Where appropriate, a security bypass function may be applied to override a disablement function and allow operation of at least one function without direct access to the security sequence required for normal operation. Criteria for such bypasses may be developed for individual embodiments.

Alternate embodiments may employ substantially the same counting algorithm as presented in the discussion of FIGS. 6 and 7, using imager heads that may not be fixed and oriented downward toward horizontal stages. Such embodiments, using ambient light, scanning lasers, or pulsed, diffused infrared, among other illuminating radiation sources, may count units at various distances from the imager heads. Applications are not limited to prescription fulfillment, nor to counting functions. In some embodiments, a principal use can be detection of defective frangible items, such as in light bulb quality control monitoring a conveyor belt. In still other embodiments, law enforcement may find uses in counting crowd populations or automobile traffic. Similarly, detection of burned-out streetlights from imagers mounted on cell phone towers, or counting whitecaps from imagers borne on aircraft as an indication of wind speed, may be feasible.

In some embodiments, processing circuitry (e.g., corresponding to processor 66 or 126) associated with the counter (e.g., 10, 32, 52, 60 or 114) may be configured to perform the image analysis and comparisons associated with the feature recognition algorithm pursuant to operation of example embodiments using an image processor 500. In this regard, for example, image processor 500, shown in the example of FIG. 11, may be configured to not only determine a number of pills disposed on a stage (e.g., stage 72), but to determine a likelihood rating that the pill (or unit 74) that is detected corresponds to the medication that has been prescribed. As such, the image processor 500 may be configured to receive image data 510 generated responsive to scanning of a tray by a camera and be further configured to compare the image data 510 to reference data 210 responsive to further processing performed by the image processor 500. The reference data 210 may include image data that has been captured on the same or a similar model machine so that the hardware used to generate the reference data is substantially similar to the hardware used to generate the image data 510. Moreover, the reference data 210 and the image data 510 may each be captured images of medications or pills that are disposed on a tray so that the pills are likely to present their widest or largest profile to the camera. The image processor 500 may determine a likelihood rating for the pill or pills in the image data 510 and pass, fail or request agent review of the pill or pills prior to clearing the pills for usage to fill the corresponding prescription.

Figure 11:
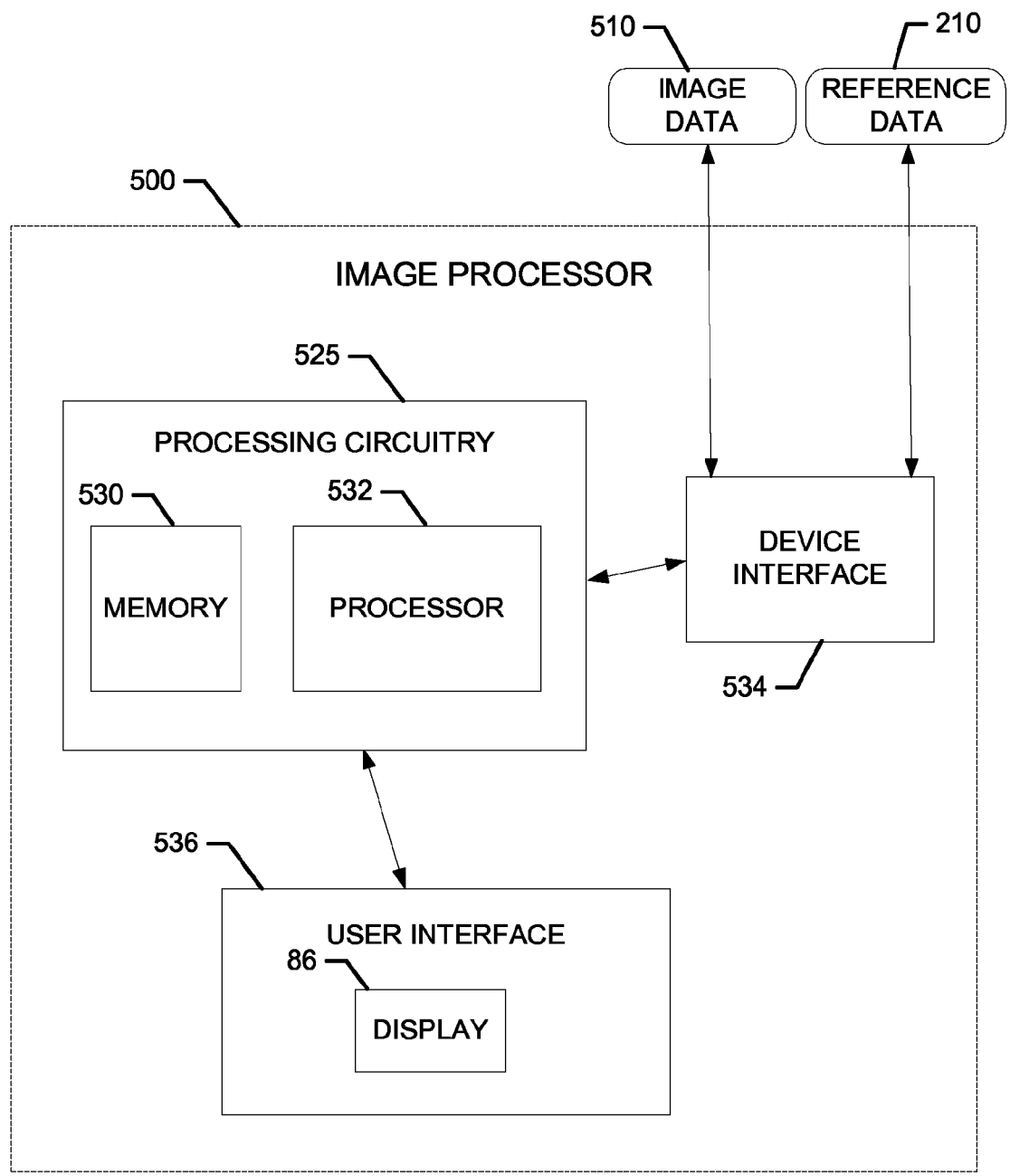
FIG. 11 illustrates a block diagram of an image processor that may be used to implement the processing described in reference to FIGS. 1-10 according to an example embodiment.

FIG. 11 illustrates a block diagram of image processor 500 that may be used to implement the processing described above (in association with processor 66 or 126), and which may be further configured to provide graphical image processing including pill counting and/or pill verification. In this regard, the image processor 500 may include processing circuitry 525 that may include a processor 530 and memory 532 that may be in communication with or otherwise control a device interface 534 and, in some cases, a user interface 536. As such, the processing circuitry 525 may be embodied as a circuit chip (e.g., an integrated circuit chip) configured (e.g., with hardware, software or a combination of hardware and software) to perform operations described herein. However, in some embodiments, the processing circuitry 525 may be embodied as a portion of an on-board computer.

The user interface 536 (if implemented) may be in communication with the processing circuitry 525 to receive an indication of a user input at the user interface 536 and/or to provide an audible, visual, mechanical or other output to the user. As such, the user interface 536 may include, for example, a display (e.g., a touch screen such as display 86), one or more buttons or keys, and/or other input/output mechanisms. In some embodiments, the user interface 536 may be provided on a panel that forms a portion of or is attached to the base unit. However, in other embodiments, the user interface 536 may be separately provided or may be provided proximate to the camera (as in FIG. 9).

The device interface 534 may include one or more interface mechanisms for enabling communication with other devices (e.g., sensors such as the camera 78 or 406). In some cases, the device interface 534 may be any means such as a device or circuitry embodied in either hardware, or a combination of hardware and software that is configured to receive and/or transmit data from/to sensors and/or input devices in communication with the image processor 500.

In an exemplary embodiment, the memory 532 may include one or more non-transitory memory devices such as, for example, volatile and/or non-volatile memory that may be either fixed or removable. The memory 532 may be configured to store information, data, applications, instructions or the like for enabling the processing circuitry 500 to carry out various functions in accordance with exemplary embodiments of the present invention. For example, the memory 532 could be configured to buffer input data for processing by the processor 530. Additionally or alternatively, the memory 532 could be configured to store instructions for execution by the processor 530. As yet another alternative, the memory 532 may include one or more databases that may store a variety of data sets responsive to input from cameras, scanners and/or the like. Among the contents of the memory 532, applications may be stored for execution by the processor 530 in order to carry out the functionality associated with each respective application. In some cases, the applications may include control applications that perform image processing to count pills and/or determine whether pills in an image are the correct pills for filling a prescription as described herein.

The processor 530 may be embodied in a number of different ways. For example, the processor 530 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor 530 may be configured to execute instructions stored in the memory 532 or otherwise accessible to the processor 532. As such, whether configured by hardware or by a combination of hardware and software, the processor 530 may represent an entity (e.g., physically embodied in circuitry—in the form of processing circuitry 500) capable of performing operations according to embodiments of the present invention while configured accordingly. Thus, for example, when the processor 530 is embodied as an ASIC, FPGA or the like, the processor 530 may be specifically configured hardware for conducting the operations described herein. Alternatively, as another example, when the processor 530 is embodied as an executor of software instructions, the instructions may specifically configure the processor 530 to perform the operations described herein.

In an example embodiment, the processor 530 (or the processing circuitry 525) may be embodied as, include or otherwise control the image processor 500 with respect to the counting and/or other image processing functions described herein. As such, in some embodiments, the processor 530 (or the processing circuitry 525) may be said to cause each of the operations described in connection with the image processor 500 by directing the image processor 500 to undertake the corresponding functionalities responsive to execution of instructions or algorithms configuring the processor 530 (or processing circuitry 525) accordingly. As an example, the image processor 500 may be configured to control image processing and/or annotation as described herein. In particular, the image processor 500 may be configured to process image data? (e.g., the received image data 510) to count each pill and/or determine whether pills in the image data are the correct pills for filling a particular prescription. In an example embodiment, pill likelihood ratings and corresponding determinations regarding whether a pill in an image is the correct pill for filling of a particular prescription may be made by employment of the feature recognition algorithm described above.

In some embodiments, a prescription number may be obtained by scanning information on a reference document such as a previously prepared prescription label (e.g., via an optical reading device, such as the barcode scanner 94). Meanwhile, the stock bottle identification information may be obtained responsive to scanning information associated with a barcode on an information label of a medication vial or bottle (e.g., via an optical reading device, such as the barcode scanner 94). Reference data may be retrieved based on the prescription label to correspond to image data of reference pills known to correspond to the prescribed medication. Image data of pills placed on the tray from the stock bottle may then be compared to the reference data as described above and a determination may be made as to whether the correct pills for the prescription are located in the tray.

Figure 12:
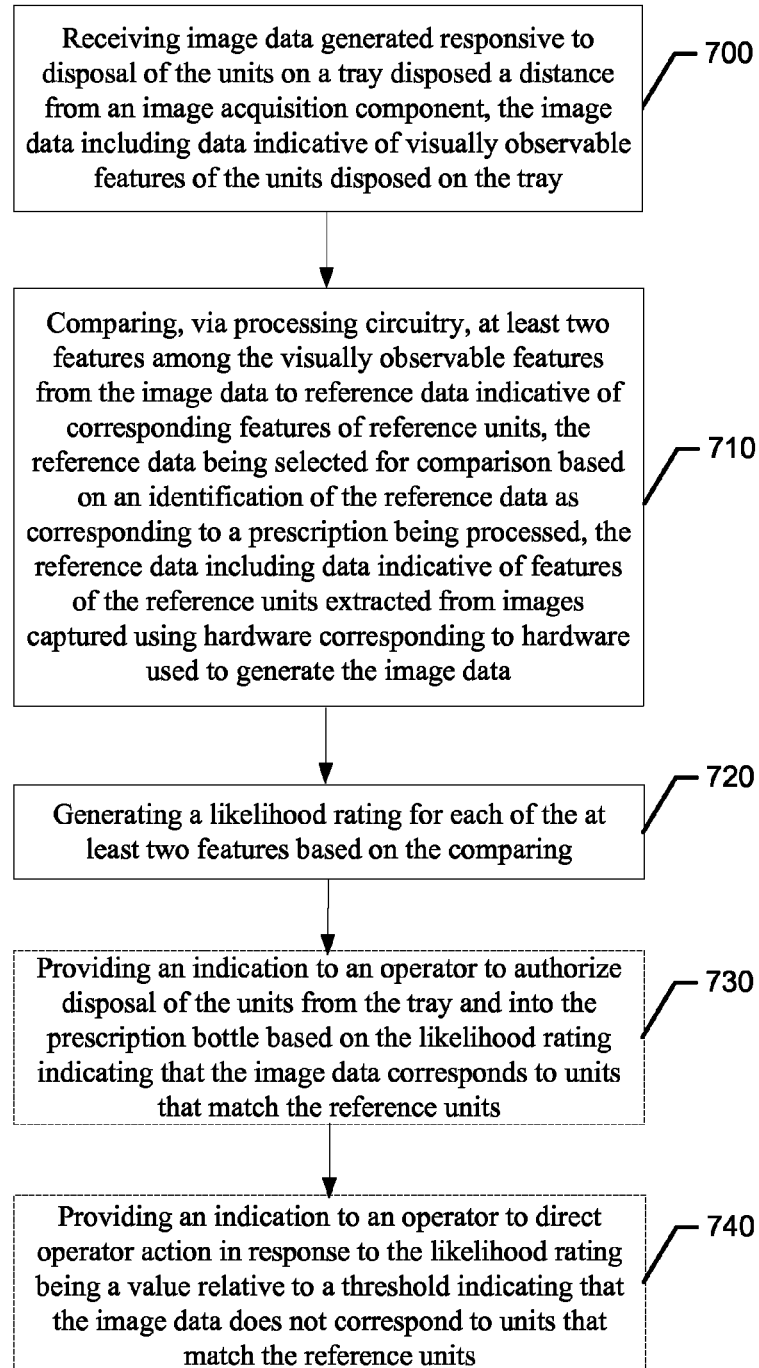
FIG. 12 is a flowchart of a system, method and program product according to example embodiments of the invention.

FIG. 12 is a flowchart of a system, method and program product according to example embodiments of the invention. It will be understood that each block of the flowchart, and combinations of blocks in the flowchart, may be implemented by various means, such as hardware, firmware, processor, circuitry and/or other device associated with execution of software including one or more computer program instructions. For example, one or more of the procedures described above may be embodied by computer program instructions. In this regard, the computer program instructions which embody the procedures described above may be stored by a memory device of an apparatus employing an embodiment of the present invention and executed by a processor in the apparatus. As will be appreciated, any such computer program instructions may be loaded onto a computer or other programmable apparatus (e.g., hardware) to produce a machine, such that the resulting computer or other programmable apparatus provides for implementation of the functions specified in the flowchart block(s). These computer program instructions may also be stored in a non-transitory computer-readable storage memory that may direct a computer or other programmable apparatus to function in a particular manner, such that the instructions stored in the computer-readable storage memory produce an article of manufacture the execution of which implements the function specified in the flowchart block(s). The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart block(s). As such, the operations of FIG. 12, when executed, convert a computer or processing circuitry into a particular machine configured to perform an example embodiment of the present invention. Accordingly, the operations of FIG. 12 define an algorithm for configuring a computer or processing circuitry 525 (e.g., processor 530) to perform an example embodiment. In some cases, a general purpose computer may be provided with an instance of the image processor 500, which performs the algorithm shown in FIG. 12 (e.g., via configuration of the processor 530), to transform the general purpose computer into a particular machine configured to perform an example embodiment.

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In this regard, one embodiment of a method for processing graphical image data representing pills or other medication related units, as shown in FIG. 12, includes receiving image data generated responsive to disposal of the units on a tray disposed a distance from an image acquisition component where the image data includes data indicative of visually observable features of the units disposed on the tray at operation 700. The method may further include comparing, e.g., via processing circuitry, at least two features among the visually observable features from the image data to reference data indicative of corresponding features of reference units at operation 710. The reference data may be selected for comparison based on an identification of the reference data as corresponding to a prescription being processed. The reference data may also include data indicative of features of the reference units extracted from images captured using hardware corresponding to hardware used to generate the image data. Hardware "corresponding" to hardware used to generate the image data may be camera equipment that is the same or substantially equivalent to the camera equipment used to obtain the reference data. As such, for example, at least the same model of counting and verification device having similar camera and/or lighting equipment disposed at the same distance from the tray in which the medication is disposed may be employed to inherently account for any differences in scale, perspective, camera resolution, lighting or other factors that may impact the images. The method may further include generating a likelihood rating for each of the at least two features based on the comparing at operation 720.

In some embodiments, certain ones of the operations above may be modified or further amplified as described below. Moreover, in some embodiments additional optional operations may also be included (an example of which is shown in dashed lines in FIG. 12). It should be appreciated that each of the modifications, optional additions or amplifications below may be included with the operations above either alone or in combination with any others among the features described herein. In an example embodiment, receiving the image data may include receiving the image data prior to filling a prescription bottle associated with the prescription. In some cases, the method may further include providing an indication to an operator to authorize disposal of the units from the tray and into the prescription bottle based on the likelihood rating indicating that the image data corresponds to units that match the reference units at operation 730 or providing an indication to an operator to direct operator action in response to the likelihood rating being a value relative to a threshold indicating that the image data does not correspond to units that match the reference units at operation 740. In some example embodiments, generating the likelihood rating may include generating a composite likelihood rating based on independently determined likelihood ratings for each of a plurality of features (e.g., where the plurality of features may include at least color, size, shape and surface markings). In some cases, generating the likelihood rating may include generating a score indicative of a degree of matching between features of the image data and corresponding features of the reference data where the score may be comparable to at least two thresholds to determine at least three classifications of likelihood ratings for the corresponding features based on comparing the score to the at least two thresholds (e.g., between the two thresholds and on opposite sides of each threshold). In an example embodiment, generating the likelihood rating may include generating a plurality of independent likelihood ratings for respective different features, and failure of a value of any one of the independent likelihood ratings to meet a threshold may cause a determination that the image data does not correspond to units that match the reference units. In some embodiments, generating the likelihood rating may include generating the likelihood rating in association with a counting operation in which the units are counted. Moreover, in some cases, both the counting operation and generating the likelihood rating may be accomplished prior to the units being removed from the tray (e.g., being transferred into a pill bottle to fill the prescription).

In an example embodiment, an apparatus for performing the method of FIG. 12 above may comprise a processing circuitry (e.g., processing circuitry 525) configured to perform some or each of the operations (700-740) described above, with or without some or all of the modifications described above. The processing circuitry 525 may, for example, be configured to perform the operations (700-740) by performing hardware implemented logical functions, executing stored instructions, or executing algorithms for performing each of the operations. Alternatively, the apparatus may comprise means for performing each of the operations described above. In this regard, according to an example embodiment, examples of means for performing operations 700-740 may comprise, for example, the image processor 500. Additionally or alternatively, at least by virtue of the fact that the processing circuitry 525 may be configured to control or even be embodied as the image processor 500, the processing circuitry 525 and/or a device or circuitry for executing instructions or executing an algorithm for processing information as described above may also form example means for performing operations 700-740.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. A method of processing graphical image data representing optically scanned medication-related units comprising:
receiving image data generated responsive to disposal of the units on a tray disposed a distance from an image acquisition component, the image data including data indicative of visually observable features of the units disposed on the tray;
comparing, via processing circuitry, at least two features among the visually observable features from the image data to reference data indicative of corresponding features of reference units, the reference data being selected for comparison based on an identification of the reference data as corresponding to a prescription being processed, the reference data including data indicative of features of the reference units extracted from images captured using hardware corresponding to hardware used to generate the image data such that the images are captured using substantially the same camera disposed the same distance from reference units in the reference data as the units on the tray; and
generating a likelihood rating for each of the at least two features based on the comparing,
wherein generating the likelihood rating comprises generating a score indicative of a degree of matching between features of the image data and corresponding features of the reference data, the score being comparable to at least two thresholds to determine at least three classifications of likelihood ratings for the corresponding features based on comparing the score to the at least two thresholds, and wherein the at least three classifications comprising at least one classification for which an automated response is provided and at least one classification for which operator intervention is solicited, and
wherein generating the likelihood rating comprises generating the likelihood rating in association with a counting operation in which the units are counted, and wherein both the counting operation and generating the likelihood rating are accomplished prior to the units being removed from the tray.

2. The method of claim 1, wherein receiving the image data comprises receiving the image data prior to filling a prescription bottle associated with the prescription.

3. The method of claim 2, further comprising providing an indication to an operator to authorize disposal of the units from the tray and into the prescription bottle based on the likelihood rating indicating that the image data corresponds to units that match the reference units.

4. The method of claim 1, further comprising providing an indication to an operator to direct operator action in response to the likelihood rating being a value relative to a threshold indicating that the image data does not correspond to units that match the reference units.

5. The method of claim 1, wherein generating the likelihood rating comprises generating a composite likelihood rating based on independently determined likelihood ratings for each of a plurality of features.

6. The method of claim 5, wherein the plurality of features include at least color, size, shape and surface markings.

7. The method of claim 1, wherein the reference data is stored locally at a device performing the comparing or remotely at a device other than the device performing the comparing.

8. A machine-vision based prescription verification device for medication-related units comprising:
a tray disposed on a base unit to receive the units;
an image acquisition component disposed a distance from the tray, the image acquisition component configured to generate image data responsive to disposal of the units on the tray, the image data including data indicative of visually observable features of the units disposed on the tray;
an image processor comprising processing circuitry configured to:
compare at least two features among the visually observable features from the image data to reference data indicative of corresponding features of reference units, the reference data being selected for comparison based on an identification of the reference data as corresponding to a prescription being processed, the reference data including data indicative of features of the reference units extracted from images captured using hardware corresponding to hardware used to generate the image data such that the images are captured using substantially the same camera disposed the same distance from reference units in the reference data as the units on the tray; and
generate a likelihood rating for each of the at least two features based on the comparison,
wherein generating the likelihood rating comprises generating a score indicative of a degree of matching between features of the image data and corresponding features of the reference data, the score being comparable to at least two thresholds to determine at least three classifications of likelihood ratings for the corresponding features based on comparing the score to the at least two thresholds, and wherein the at least three classifications comprising at least one classification for which an automated response is provided and at least one classification for which operator intervention is solicited, and
wherein the processing circuitry being configured to generate the likelihood rating comprises the processing circuitry being configured to generate the likelihood rating in association with a counting operation in which the units are counted, and wherein both the counting operation and generating the likelihood rating are accomplished prior to the units being removed from the tray.

9. The device of claim 8, wherein the processing circuitry being configured to receive the image data comprises the processing circuitry being configured to receive the image data prior to filling a prescription bottle associated with the prescription.

10. The device of claim 9, wherein the processing circuitry is further configured to provide an indication to an operator to authorize disposal of the units from the tray and into the prescription bottle based on the likelihood rating indicating that the image data corresponds to units that match the reference units.

11. The device of claim 8, wherein the processing circuitry is further configured to provide an indication to an operator to direct operator action in response to the likelihood rating being a value relative to a threshold indicating that the image data does not correspond to units that match the reference units.

12. The device of claim 8, wherein the processing circuitry being configured to generate the likelihood rating comprises the processing circuitry being configured to generate a composite likelihood rating based on independently determined likelihood ratings for each of a plurality of features.

13. The device of claim 12, wherein the plurality of features include at least color, size, shape and surface markings.

14. The device of claim 8, wherein the reference data is stored locally at a device performing the comparing or remotely at a device other than the device performing the comparing.

15. A computer program product for processing graphical image data representing optically scanned medication-related units, the computer program product comprising at least one non-transitory computer-readable storage medium having computer-executable program code instructions stored therein, the computer-executable program code instructions comprising program code instructions for:

receiving image data generated responsive to disposal of the units on a tray disposed a distance from an image acquisition component, the image data including data indicative of visually observable features of the units disposed on the tray;

comparing, via processing circuitry, at least two features among the visually observable features from the image data to reference data indicative of corresponding features of reference units, the reference data being selected for comparison based on an identification of the reference data as corresponding to a prescription being processed, the reference data including data indicative of features of the reference units extracted from images captured using hardware corresponding to hardware used to generate the image data such that the images are captured using substantially the same camera disposed the same distance from reference units in the reference data as the units on the tray; and generating a likelihood rating for each of the at least two features based on the comparing, wherein generating the likelihood rating comprises generating a score indicative of a degree of matching between features of the image data and corresponding features of the reference data, the score being comparable to at least two thresholds to determine at least three classifications of likelihood ratings for the corresponding features based on comparing the score to the at least two thresholds, and wherein the at least three classifications comprising at least one classification for which an automated response is provided and at least one classification for which operator intervention is solicited, and wherein the processing circuitry being configured to generate the likelihood rating comprises the processing circuitry being configured to generate the likelihood rating in association with a counting operation in which the units are counted, and wherein both the counting operation and generating the likelihood rating are accomplished prior to the units being removed from the tray.

16. The computer program product of claim 15, further comprising computer program code for storing the annotated image in a memory to enable future retrieval of the annotated image.

* * * * *